(12) United States Patent
Burchfield

(10) Patent No.: US 9,057,699 B2
(45) Date of Patent: Jun. 16, 2015

(54) HIGH TEMPERATURE DIFFERENTIAL ION MOBILITY SPECTROSCOPY

(71) Applicant: Hamilton Sundstrand Corporation, Charlotte, NC (US)

(72) Inventor: David E. Burchfield, Alta Loma, CA (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 0 days.

(21) Appl. No.: 14/184,267

(22) Filed: Feb. 19, 2014

(65) Prior Publication Data

US 2015/0136974 A1    May 21, 2015

Related U.S. Application Data

(60) Provisional application No. 61/907,213, filed on Nov. 21, 2013.

(51) Int. Cl.
*H01J 49/00* (2006.01)
*H01J 49/40* (2006.01)
*B01D 59/44* (2006.01)
*G01N 27/64* (2006.01)
*G01N 27/62* (2006.01)
*H01J 49/26* (2006.01)
*H01J 49/04* (2006.01)

(52) U.S. Cl.
CPC .............. *G01N 27/624* (2013.01); *H01J 49/26* (2013.01); *H01J 49/0422* (2013.01); *H01J 49/049* (2013.01)

(58) Field of Classification Search
CPC ... G01N 27/622; G01N 27/624; G01N 27/64; H01J 49/165
USPC ........................ 250/288, 281, 282, 283, 287
See application file for complete search history.

(56) References Cited

U.S. PATENT DOCUMENTS

| 7,863,562 | B2 | 1/2011 | Wollnik et al. |
| 7,943,901 | B2 | 5/2011 | Wu |
| 8,138,474 | B2 | 3/2012 | Wollnik et al. |
| 8,502,138 | B2 | 8/2013 | Matthews et al. |
| 8,536,518 | B2 | 9/2013 | Kozole |
| 8,754,366 | B2 * | 6/2014 | Burchfield et al. ........... 250/287 |

(Continued)

FOREIGN PATENT DOCUMENTS

WO    WO 2004/081527 A2    9/2004

*Primary Examiner* — Nikita Wells
(74) *Attorney, Agent, or Firm* — Kinney & Lange, P.A.

(57) ABSTRACT

In a first embodiment, a spectroscopy device comprises a preheater, an ionizer, and a differential ion mobility spectroscopy (DMS) analyzer. The preheater is disposed to heat inlet air to 150° C. or more. The ionizer is disposed to receive and ionize heated inlet air from the preheater. The differential ion mobility spectroscopy (DMS) analyzer has a reception element configured to detect ionized chemical agents in the inlet air.

In a second embodiment, a spectroscopy device comprises a DMS detector and a controller. The DMS detector comprises an ionizer disposed to receive and ionize inlet air at 150° C. or more, and an analyzer disposed to selectively receive ions from the ionizer under varying radio frequency voltage and compensation field voltage. The controller is configured to flag at least one chemical agent as present in the inlet air upon reception of negatively charged ions by the analyzer under corresponding values of the radio frequency voltage and the compensation field voltage.

15 Claims, 3 Drawing Sheets

(56) References Cited

U.S. PATENT DOCUMENTS

| | | | |
|---|---|---|---|
| 2005/0051719 A1* | 3/2005 | Miller et al. | 250/287 |
| 2010/0001182 A1 | 1/2010 | Burchfield et al. | |
| 2013/0062517 A1* | 3/2013 | Shvartsburg et al. | 250/282 |
| 2013/0092834 A1 | 4/2013 | Covey et al. | |
| 2013/0211211 A1* | 8/2013 | Sato | 600/309 |

* cited by examiner

HIGH TEMPERATURE DIFFERENTIAL ION MOBILITY SPECTROSCOPY

CROSS-REFERENCE TO RELATED APPLICATION

This application claims priority to U.S. provisional application Ser. No. 61/907,213, entitled "HIGH TEMPERATURE DIFFERENTIAL ION MOBILITY SPECTROSCOPY," filed Nov. 21, 2013, which is hereby incorporated by reference in its entirety.

BACKGROUND

The present invention relates generally to chemical detector systems, and more specifically to systems using differential ion mobility spectroscopy.

Systems for the detection of airborne chemicals are commonly used to sense the presence of chemical warfare agents such as mustards and nerve agents. Such systems must be capable of accurately and reliably detecting and identifying dangerous chemicals in very low concentrations, and in a variety of environments. Man-portable versions of such systems are used by soldiers and engineers to identify possible hazards in the field.

Many fielded chemical warfare agent detectors use one variety or another of ion mobility spectroscopy (IMS). IMS-based detectors ionize incoming gases at an ionizer that feeds the ionized gases into an analyzer. Conventional devices include both time-of-flight based IMS analyzers, and differential ion mobility spectroscopy (DMS) analyzers. Field asymmetric ion mobility spectroscopy (FAIMS) devices are DMS systems that utilize analyzers with asymmetric radio frequency fields to selectively pass ions of particular volume and charge to a reception element such as a biased Faraday collector. Recently developed rapid thermal IMS (RTIMS) systems utilize DMS techniques with micro-scale analyzer structures, allowing RTIMS instruments to achieve stronger fields.

IMS systems have low tolerances for humidity. To remove water from sample air, many fielded DMS systems use dehumidification loops whereby inlet air is mixed with dry air and recirculated through or past one or more consumable ceramic sorbent or chemical desiccant elements. Recirculation systems are power intensive, and desiccant elements may need to be replaced often in high-humidity environments.

SUMMARY

In a first embodiment, the present invention relates to a spectroscopy device comprising a preheater, an ionizer, and a differential ion mobility spectroscopy (DMS) analyzer. The preheater is disposed to heat inlet air to 150° C. or more. The ionizer is disposed to receive and ionize heated inlet air from the preheater. The differential ion mobility spectroscopy (DMS) analyzer has a receiver element configured to detect ionized chemical agents in the inlet air.

In a second embodiment, the present invention relates to a spectroscopy device comprising a DMS detector and a controller. The DMS detector comprises an ionizer disposed to receive and ionize inlet air at 150° C. or more, and an analyzer disposed to selectively receive ions from the ionizer under varying radio frequency voltage and compensation field voltage. The controller is configured to flag at least one chemical agent as present in the inlet air upon reception of positively or negatively charged ions by the analyzer under corresponding values of the radio frequency voltage and the compensation field voltage.

DETAILED DESCRIPTION

Figure 1:
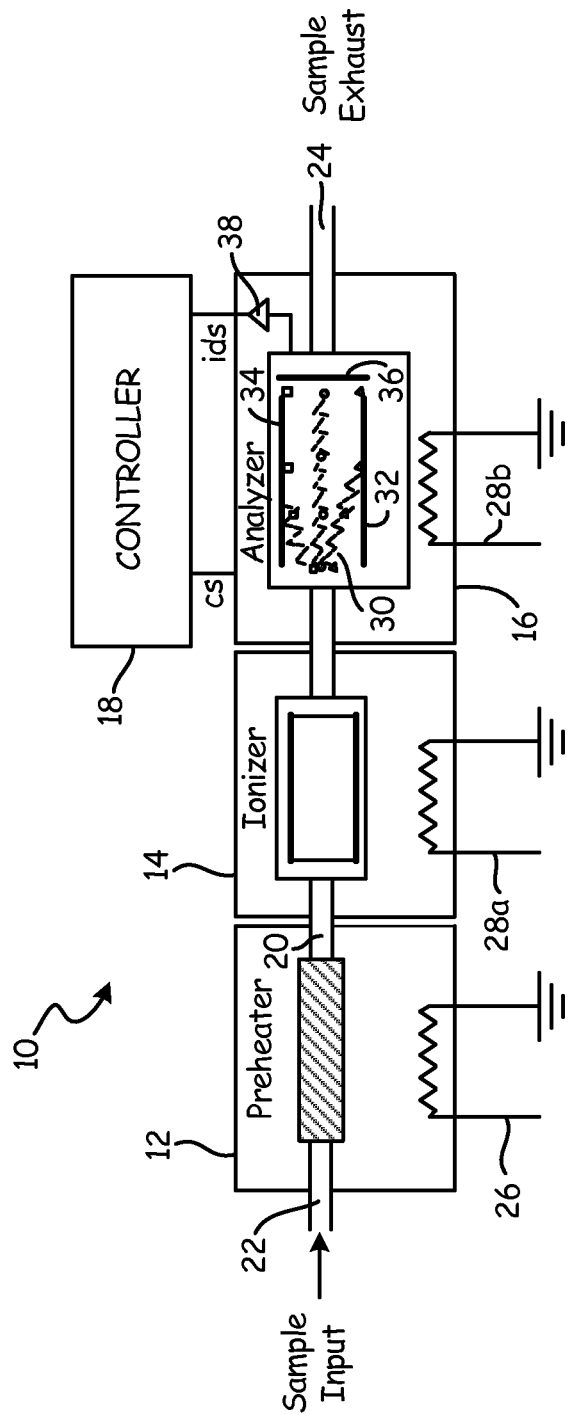
FIG. 1 is a schematic view of a differential ion mobility spectroscopy (DMS) device comprising a direct air preheater, a DMS detector, and a controller.

FIG. 1 is a schematic view of spectroscopy device 10, comprising preheater 12, ionizer 14, analyzer 16, and controller 18. Air passage 20 carries sample air from sample input 22 through preheater 12, ionizer 14, and analyzer 16 to sample exhaust 24. Preheater 12 includes primary heating element 26. In some embodiments, ionizer 14 and analyzer 16 may include secondary heating elements 28a and 28b, respectively. Analyzer 16 includes field chamber 30, which is bounded by ground plate 32 and radio-frequency (RF) plate 34, and terminates at reception element 36. Amplifier 38 receives and amplifies the voltage output of reception element 36, and provides resulting ion detection signal ids to controller 18. Controller 18 modulates electric fields within field chamber 30 via control signal cs.

Sample gases enter spectroscopy device 10 via sample input 22 in preheater 12. Preheater 12 heats these sample gases to at least 150° C. via primary heating element 26. Although primary heating element 26 is illustrated in FIG. 1 as a resistive heater, other types of heating may equivalently be used, including chemical or radiant (i.e., infrared or microwave) heating systems. In some embodiments, air passage 20 may follow a tortuous or divided path through preheater 12 to maximize sample gas exposure to primary heating element 26. Preheater 12 is a direct inlet heater that does not recirculate sample air, but rather receives gas directly from sample input 22 and provides gas directly to ionizer 14.

Ionizer 14 and analyzer 16 together comprise a differential ion mobility (DMS) detector that detects and identifies particular chemicals within sample gases from sample input 22. Ionizer 14 is a device disposed to deposit charge on molecules of sample gases. Ionizer 14 may, for instance, include a corona discharge device or a radioactive source such as a plate or element of Am-241 or Ni-64. Secondary heating elements 28a and 28b may be included to maintain the temperature (>150° C.) set by primary heating element 26 of preheater 12.

Ionizer 14 provides thermal electrons with an energy distribution in part determined by gas temperature. Analyzer 16 receives sample gas from ionizer 14, including at least a subset of ionized gas molecules. As described in greater detail below with respect to FIGS. 2 and 3, analyzer 16 is an air capacitor that asymmetrically deflects ionized gases under the RF field determined by an asymmetric drive wavefunction (ADW) set by controller 18 and applied to RF plate 34. This ADW comprises an RF component voltage (RFV) and a compensation field voltage (CFV). A majority of ions entering analyzer 16 are deflected by the ADW into ground plate 32 or RF plate 34, and accordingly lose their charge. Ions with a volume and charge falling within a narrow pass band determined by the RFV and the CFV are able to pass through chamber 30 without losing their charge, and are received by receiver element 36. Receiver element 36 produces a voltage signal when struck by charged particles, and may, for example, be a positively-based Faraday collector. In other embodiments, receiver element 36 may comprise both positively- and negatively-biased charge collectors, or may be alternatively biased positively and negatively to detect both positive and negative ions passing through analyzer 16. The voltage signal from receiver element 36 is amplified by amplifier 38, and transmitted as ion detection signal ids to controller 18.

Controller 18 is a logic-capable device with machine readable memory. Controller 18 may, for instance, be a printed wiring board structure with a microprocessor and solid state data storage. Alternatively, controller 18 may comprise a plurality of separate devices which cooperate to perform the functions described herein. Controller 18 includes a signature library mapping particular values or ranges of RFV and CFV to chemical ion species that might impact receiver element 36. This signature library may, for example, comprise a two- or three-dimensional lookup table by the RFV, the CFV, and (in some embodiments) the charge of the received ion.

Controller 18 is disposed to control analyzer 16 via control signal cs, and to analyze detection events from analyzer 16 based on ion detection signal ids. Control signal cs sets the RFV and CFV applied to RF plate 34. The RFV and CFV together define a two-dimensional parameter space occupied by a wide range of possible detection events. In some embodiments, controller 18 may cycle through a range of values of the RFV and CFV to fully traverse an area of this parameter space corresponding to every signature mapped in the signature library. Controller 18 logs the RFV and CFV currently specified by control signal cs whenever ion detection signal ids indicates that an ion has been received by receiver element 38. This log is checked against the signature library to identify the triggering ion species received at receiver element 36. In some embodiments, controller 18 may flag an alarm state if the ion species corresponds to a dangerous chemical agent. Some embodiments of controller 18 may store a history of particle identifications, either for later archiving or to flag an alarm state if a threshold number of dangerous chemical agent identifications are made within a set time period.

Figure 2:
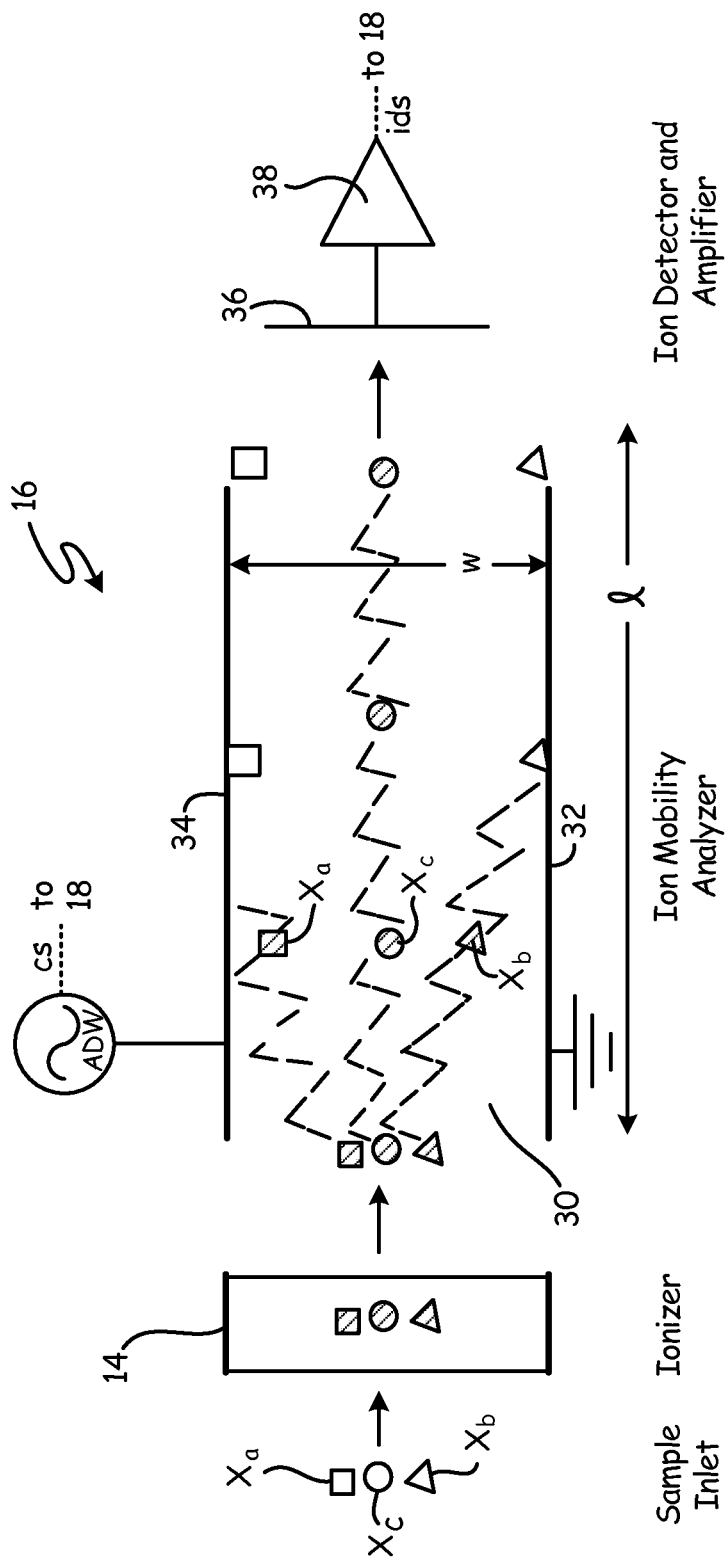
FIG. 2 is schematic view of the DMS detector of FIG. 1.
Figure 3:
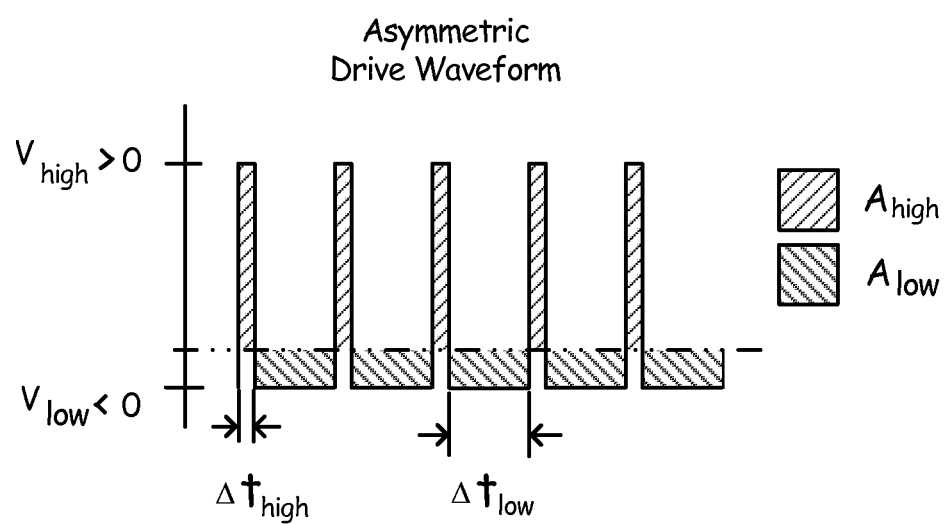
FIG. 3 is a graph of an example drive waveform for the DMS detector of FIG. 2.

FIGS. 2 and 3 describe the behavior of spectroscopy device 10 during operation. FIG. 2 is a schematic view of ionizer 14 and analyzer 16. FIG. 2 illustrates the passage of sample gas molecules $X_a$, $X_b$, and $X_c$ through ionizer 14, into chamber 30, to ground plate 32, RF plate 34, or reception element 36. As discussed above with respect to FIG. 1, reception element 36 outputs to amplifier 38, which provides ion detection signal ids to controller 18. Ground plate 32 is held at a constant ground potential, while plate 34 receives a varying ADW voltage specified by control signal cs. FIG. 3 is a graph of one possible embodiment of this ADW voltage as a function of time, illustrating low potential period $\Delta t_{low}$, high potential period $\Delta t_{high}$, low voltage $V_{low}$, high voltage $V_{high}$, low voltage area $\Delta t_{low}$, and high voltage area $A_{high}$. $Low\ voltage\ Vlow$ and high voltage $V_{high}$ represent the lower and upper voltage bounds of the ADW, respectively, while low potential period $\Delta t_{low}$ and high potential period $\Delta t_{high}$ represent continuous duration spent at low voltage $V_{low}$ and high voltage $V_{high}$, respectively. Low voltage area $A_{low}$ and high voltage area $A_{high}$ are areas under the ADW curve, and represent time-weighted potential during low potential period $\Delta t_{low}$ and high potential period $\Delta t_{high}$, respectively.

Although FIG. 2 depicts all three sample gas molecules $X_a$, $X_b$, and $X_c$ as electrically charged (shaded) upon passing through ionizer 14, a person skilled in the art will understand that the majority of gas molecules passing through spectroscopy device 10 will remain uncharged, and will accordingly not be registered by reception element 36. Only the minority of gas molecules charged by ionizer 14 are of interest in the operation of reception element 36 and controller 18. In general, the more thermal electrons provided by ionizer 14, the greater the proportion of sample gas that will enter analyzer 16 as ions, and the greater the sensitivity of spectroscopy device 10.

As shown in FIG. 2, gas molecules $X_a$, $X_b$, and $X_c$ follow zig-zagging trajectories under the influence of the varying electric fields applied within chamber 30 by the ADW. As illustrated in FIG. 3, the ADW applied to RF plate 34 is a step function alternating between relatively short duration maxima at high voltage $V_{high}$, over high potential period $\Delta t_{high}$, and relatively long duration minima at low voltage $V_{low} < V_{high}$, over low potential period $\Delta t_{low} > \Delta t_{high}$. The total voltage difference between low and high voltages $V_{low}$ and $V_{high}$, respectively, constitutes the radio frequency component voltage (RFV) referred to above with respect to FIG. 1, while the displacement of low voltage $V_{low}$ with respect to the ground defined by ground plate 32 constitutes the compensation field voltage (CFV). As shown schematically in FIG. 2, a negatively charged ion under the influence of the electric field applied by the ADW is attracted steeply towards RF plate 34 during high potential period $\Delta t_{high}$, and repelled more gradually away from RF plate 34 during low potential period $\Delta t_{high}$. Low voltage area $A_{low}$ and high voltage area $A_{high}$ roughly correspond to the net displacement of negatively charged ions towards ground plate 32 and RF plate 34, respectively during the two portions of each cycle. Ions of different cross-sections exhibit different characteristic differential mobility under variable fields, causing different chemical agents to experience different drift towards ground plate 32 or RF plate 34, over multiple cycles of the ADW. As illustrated in FIG. 2, gas molecule $X_a$ has greater mobility during high potential periods $\Delta t_{high}$, and accordingly drifts towards RF plate 34. By contrast, gas molecule $X_b$ has greater mobility during low potential periods $\Delta t_{low}$, and accordingly drifts towards ground plate 32. For each ion species, some configuration of the RFV and the CFV will allow that chemical to pass unimpeded through chamber 30. The arrival of an ion at reception element 36 thus indicates the presence of particular molecule that controller 18 identifies by comparing these RFV and CFV values with entries in the signature library. By cycling through a range of ADW shapes, controller is able to test for the presence of a wide range of chemical agents in sample gases.

The present invention is applicable to several different types of DMS methods. Applied to traditional DMS methods, analyzer 16 and controller 18 operate by controlling the differential mobility of chemical agent ions as they bond and de-bond to water molecules under the influence of varying fields. Applied to RTIMS, analyzer 16 and controller 18 operate by control the differential mobility of chemical agents as a result of swelling under varying fields. RTIMS systems are generally more compact, and allow for stronger fields. In general, higher electric fields $V_{high}$ of approximately 10,000 V/cm or more ensures that the rebonding time of water molecules to gas ions will be greater than low potential period $\Delta t_{low}$, thereby preventing such bonding from throwing off the results of an RTIMS system. In one embodiment, analyzer 16 is an RTIMS analyzer with a width w of 30-50 μm and a length l of 100 μm or more. In general, a longer lengths l allow for higher resolution at the cost of reduced device throughput.

Although IMS systems are used to detect a variety of chemical warfare agents, nerve agents such as V-agents (VX, VR, etc.) and G-agents (e.g. GB) are particularly dangerous even in small concentrations, and are therefore of particular importance to detect. These phosphonate and phosphonothioate esters can undergo two possible ionization reactions:

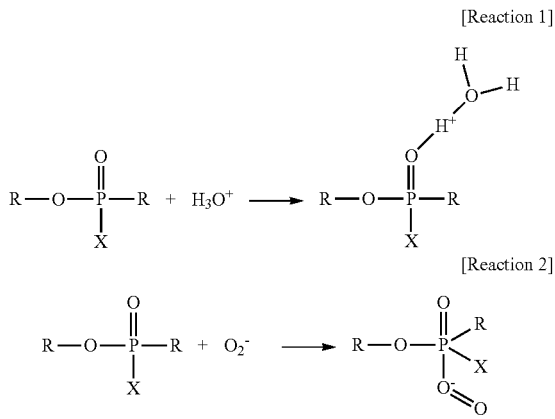

Reaction 1 produces a positively charged ester ion detected in many conventional IMS devices, and has sufficiently low activation energy to be easily obtained at conventional operating temperatures. Reaction 2, in contrast, produces a negatively charged ester ion, but has considerably higher activation energy (~3.4 kJ/mol), and is accordingly only produced in detectable quantities at temperatures of 150° C. or more. Convention DMS systems, by contrast, operate well below the critical temperature of Reaction 2. The present invention heats inlet sample gas to 150° C. or more via primary heating element 26, and maintains this temperature via secondary heating elements 28a and 28b, thereby producing negatively charged ester ion species that are received at reception element 36. Large environmental ions that are a challenge to distinguish from phosphonate ester ions are typically positively charged. Accordingly, the negatively charged ion species created in reaction 2 allow controller 18 to more accurately and precisely identify probable nerve agents among sample gases. Controller 18 is programmed to operate the detector to sense one or both of the positively charged species produced by Reaction 1, and negatively charged species produced by Reaction 2. The signature database of controller 18 includes entries for negative species of phosphonate ester ions produced by Reaction 2, such that controller 18 is able to detect, identify, and flag the presence of phosphonate ester compounds in sample air based on reception of negatively charged ion species by receiver element 36 of analyzer 16, under corresponding values of the RFV and CFV.

In addition to providing the critical activation energy for Reaction 2, above, the high inlet gas temperature (≥150° C.) provided by preheater 12 and maintained by secondary heating elements 28a and 28b allows spectroscopy device 10 to handle relatively high humidity without need for the air recirculation loops or consumable desiccants common among fielded IMS devices. RTIMS systems depend on the suppression of cluster formation with water molecules, and as a result are highly sensitive to moisture. At room temperatures, conventional RTIMS systems can tolerate only ~0.2% water vapor by volume in sample air. At temperatures of 150-200° C., by contrast, analyzer 16 can tolerate ~3% water vapor by volume. Heating sample gases to at least 150° C. thus obviates the need for additional dehumidification devices during ordinary operating conditions, with two significant results. First, spectroscopy device 10 is not dependent on consumable desiccant or sorbent packs to function in humid environments. Second, spectroscopy device 10 does not need a drying recirculation system. Recirculation loops and fans account for approximately half of the power draw much of the weight and bulk of many fielded IMS devices. By operating at sufficiently high temperatures (≥150° C.), spectroscopy device 10 is able to dispense with these components, reducing the overall weight and increasing the power efficiency and battery life of the system. Recirculation loops also dramatically dilute sample air, sometimes by a factor of ten or more. Preheater 12 draws sample air directly from the environment and provides heated air directly to ionizer 14, thus avoiding this dilution and increasing the overall sensitivity of spectroscopy device 10.

The present invention includes both heating elements to hold sample gases at or above the critical temperature of 150° C. (see preheater 12, primary heating element 26, and secondary heating elements 28a and 28b, described above with respect to FIG. 1), and a processor capable of identifying nerve agents based on reception of the resulting negatively charged phosphonate ester ions produced in Reaction 2 (see controller 18, FIG. 1). This invention improves system sensitivity by enabling the detection of negatively charged ester ions and avoiding sample gas dilution for dehumidification, reduces the weight, bulk, and power draw of spectroscopy system 10 by eschewing recirculation systems, and avoids dependency on consumable desiccants.

Discussion of Possible Embodiments

The following are non-exclusive descriptions of possible embodiments of the present invention.

A spectroscopy device comprises: a preheater disposed to heat inlet air to 150° C. or more; an ionizer disposed to receive and ionize heated inlet air from the preheater; and a differential ion mobility spectroscopy (DMS) analyzer with a reception element configured to detect ionized chemical agents in the inlet air.

The spectroscopy device of the preceding paragraph can optionally include, additionally and/or alternatively, any one or more of the following features, configurations and/or additional components:

A further embodiment of the foregoing spectroscopy device, wherein the ionized chemical agents detected by the reception element are negatively charged chemical agent ions.

A further embodiment of the foregoing spectroscopy device, wherein the detector element is a positively biased Faraday collector.

A further embodiment of the foregoing spectroscopy device, wherein the negatively charged chemical agent ions detected by the DMS analyzer are negatively charged phosphonate esters.

A further embodiment of the foregoing spectroscopy device, wherein the DMS analyzer is characterized by a radio frequency voltages and compensation field voltages, and further comprising a controller configured to detect and identify particular chemical agents in the inlet air by correlating reception of negatively charged ions with the radio frequency voltages and the compensation field voltages.

A further embodiment of the foregoing spectroscopy device, wherein the controller is further configured to sweep through the analyzer through a range of radio frequency voltages and the compensation field voltages, in cycles.

A further embodiment of the foregoing spectroscopy device, wherein the ionizer and the DMS analyzer each comprise secondary heaters configured to maintain the inlet air at or above 150° C.

A further embodiment of the foregoing spectroscopy device, wherein the direct air preheater receives inlet air directly from a detection environment, and supplies the heated inlet air directly to the ionizer.

A further embodiment of the foregoing spectroscopy device, wherein the analyzer comprises a rapid thermal ion mobility spectroscopy micro-channel analyzer.

A spectroscopy device comprising: a differential ion mobility spectroscopy (DMS) detector comprising: an ionizer disposed to receive and ionize inlet air at 150° C. or more; and an analyzer disposed to selectively receive ions from the ionizer under varying radio frequency voltage and compensation field voltage; and a controller configured to flag at least one chemical agent as present in the inlet air upon reception of negatively charged ions by the analyzer under corresponding values of the radio frequency voltage and the compensation field voltage.

The spectroscopy device of the preceding paragraph can optionally include, additionally and/or alternatively, any one or more of the following features, configurations and/or additional components:

A further embodiment of the foregoing spectroscopy device, further comprising a signature library mapping values of radio frequency voltage and compensation field voltage to particular chemical agents, and wherein the controller is configured to flag a particular chemical agent as present in the inlet air when negatively charged ions are received by the analyzer under values of the radio frequency voltage and the compensation field voltage mapped by the signature library to that chemical agent.

A further embodiment of the foregoing spectroscopy device, wherein the controller is further configured to vary the radio frequency voltage and the compensation field voltage so as to cycle through a coordinate space corresponding covering the full range of values stored in the signature library.

A further embodiment of the foregoing spectroscopy device, wherein the analyzer is a micro-channel device with a channel thickness of 30-50 µm.

A further embodiment of the foregoing spectroscopy device, wherein the analyzer is a rapid thermal ion mobility spectroscopy analyzer.

A further embodiment of the foregoing spectroscopy device, further comprising a preheater disposed to receive and heat the inlet air to 150° C. or more, and feed the heated inlet air to the ionizer.

A further embodiment of the foregoing spectroscopy device, wherein the preheater receives the inlet air directly from a detection environment, and feeds the heated inlet air directly to the ionizer.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A spectroscopy device comprising:
a preheater disposed to heat inlet air to 150° C. or more;
an ionizer disposed to receive and ionize heated inlet air from the preheater; and
a differential ion mobility spectroscopy (DMS) analyzer with a reception element configured to detect ionized chemical agents in the inlet air; wherein the DMS analyzer is characterized by radio frequency voltages and compensation field voltages, and further comprising a controller configured to detect and identify particular chemical agents in the inlet air by correlating reception of negatively charged ions with the radio frequency voltages and the compensation field voltages.

2. The spectroscopy device of claim 1, wherein the ionized chemical agents detected by the reception element are negatively charged chemical agent ions.

3. The spectroscopy device of claim 2, wherein the detector element is a positively biased Faraday collector.

4. The spectroscopy device of claim 2, wherein the negatively charged chemical agent ions detected by the DMS analyzer are negatively charged phosphonate esters.

5. The spectroscopy device of claim 1, wherein the controller is further configured to sweep the analyzer through a range of radio frequency voltages and the compensation field voltages, in cycles.

6. The spectroscopy device of claim 1, wherein the ionizer and the DMS analyzer each comprise secondary heaters configured to maintain the inlet air at or above 150° C.

7. The spectroscopy device of claim 1, wherein the preheater receives inlet air directly from a detection environment, and supplies the heated inlet air directly to the ionizer.

8. The spectroscopy device of claim 1, wherein the analyzer comprises a rapid thermal ion mobility spectroscopy micro-channel analyzer.

9. A spectroscopy device comprising:
a differential ion mobility spectroscopy (DMS) detector comprising:
an ionizer disposed to receive and ionize inlet air at 150° C. or more; and
an analyzer disposed to selectively receive ions from the ionizer under varying radio frequency voltage and compensation field voltage; and
a controller configured to flag at least one chemical agent as present in the inlet air upon reception of negatively charged ions by the analyzer under corresponding values of the radio frequency voltage and the compensation field voltage.

10. The spectroscopy device of claim 9, further comprising a signature library mapping values of radio frequency voltage and compensation field voltage to particular chemical agents, and wherein the controller is configured to flag a particular chemical agent as present in the inlet air when negatively charged ions are received by the analyzer under values of the radio frequency voltage and the compensation field voltage mapped by the signature library to that chemical agent.

11. The spectroscopy device of claim 9, wherein the controller is further configured to vary the radio frequency voltage and the compensation field voltage so as to cycle through a coordinate space corresponding covering the full range of values stored in the signature library.

12. The spectroscopy device of claim 9, wherein the analyzer is a micro-channel device with a channel thickness of 30-50 µm.

13. The spectroscopy device of claim 12, wherein the analyzer is a rapid thermal ion mobility spectroscopy analyzer.

14. The spectroscopy device of claim 9, further comprising a preheater disposed to receive and heat the inlet air to 150° C. or more, and feed the heated inlet air to the ionizer.

15. The spectroscopy device of claim 14, wherein the preheater receives the inlet air directly from a detection environment, and feeds the heated inlet air directly to the ionizer.

* * * * *